(12) United States Patent
Bates

(10) Patent No.: US 8,562,509 B2
(45) Date of Patent: Oct. 22, 2013

(54) VENTRICULAR ASSIST DEVICE

(75) Inventor: Brian Bates, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 12/982,588

(22) Filed: Dec. 30, 2010

(65) Prior Publication Data

US 2012/0172654 A1  Jul. 5, 2012

(51) Int. Cl.
*A61N 1/362* (2006.01)
(52) U.S. Cl.
USPC .......................................................... 600/16
(58) Field of Classification Search
USPC .......................................................... 600/16
See application file for complete search history.

(56) References Cited

U.S. PATENT DOCUMENTS

| | | | |
|---|---|---|---|
| 5,755,748 A | 5/1998 | Borza | |
| 5,776,190 A | 7/1998 | Jarvik | |
| 5,888,241 A | 3/1999 | Jarvik | |
| 6,015,272 A | 1/2000 | Antaki et al. | |
| 6,264,635 B1 | 7/2001 | Wampler | |
| 6,397,109 B1 * | 5/2002 | Cammilli et al. | 607/123 |
| 6,527,699 B1 | 3/2003 | Goldowsky | |
| 6,533,716 B1 | 3/2003 | Schmitz-Rode et al. | |
| 6,685,621 B2 | 2/2004 | Bolling et al. | |
| 6,846,168 B2 | 1/2005 | Davis | |
| 7,022,100 B1 | 4/2006 | Aboul-Hosn et al. | |
| 7,125,376 B2 | 10/2006 | Viole et al. | |
| 7,144,364 B2 | 12/2006 | Barbut et al. | |
| 7,144,365 B2 | 12/2006 | Bolling et al. | |
| 7,238,151 B2 | 7/2007 | Frazier | |
| 2002/0193828 A1 * | 12/2002 | Griffin et al. | 606/200 |
| 2006/0036127 A1 * | 2/2006 | Delgado, III | 600/16 |

OTHER PUBLICATIONS

Mark D. Rodefeld, M.D., Steven H. Frankel, Ph.D., *Percutaneous Expandable Rotary Blood Pumps* [PowerPoint Presentation].

\* cited by examiner

*Primary Examiner* — Niketa Patel
*Assistant Examiner* — William Levicky
(74) *Attorney, Agent, or Firm* — Brinks Hofer Gilson & Lione

(57) ABSTRACT

A ventricular assist device includes an intravascular blood pump and a collapsible frame. The collapsible frame receives the blood pump therein and is movable between a collapsed state and an expanded state. The collapsible frame engages an interior wall of a body cavity when in the expanded state and is retrievable from the body cavity in the collapsed state.

14 Claims, 7 Drawing Sheets

VENTRICULAR ASSIST DEVICE

FIELD

The present invention relates to medical devices, and more particularly to implantable ventricular assist devices.

BACKGROUND

Ventricular assist devices are mechanical blood pumps to supplement the pumping action of the heart when the heat lacks sufficient pumping capacity to meet the needs of the body. Ventricular assist devices generally include blood pumps that deliver substantial blood flow at a pressure corresponding to normal blood pressure. The ventricular assist devices are implanted and remain in operation temporarily or permanently in patients' bodies.

Ventricular assist devices, due to their frequent mechanical action, may cause serious harm to the patient if not designed properly. For example, the mechanical action of the ventricular assist devices may lead to hemolysis, or rupture of the red blood cells in the blood. Clot may be formed when blood comes into contact with artificial surfaces of the ventricular assist devices.

SUMMARY

In one form, the ventricular assist device in accordance with the teachings of the present disclosure includes an intravascular blood pump and a collapsible frame. The collapsible frame receives the intravascular blood pump therein and is movable between a collapsed state and an expanded state. In other features, the collapsible frame engages an interior wall of a body cavity when in the expanded state and is retrievable from the body cavity in the collapsed state.

In another form, a method of retrieving a ventricular assist device includes inserting a retrieval device into a body cavity and collapsing the ventricular assist device within the retrieval device.

Further features and advantages of the invention will become readily apparent from the following description and from the claims.

DRAWINGS

DETAILED DESCRIPTION

Figure 1:
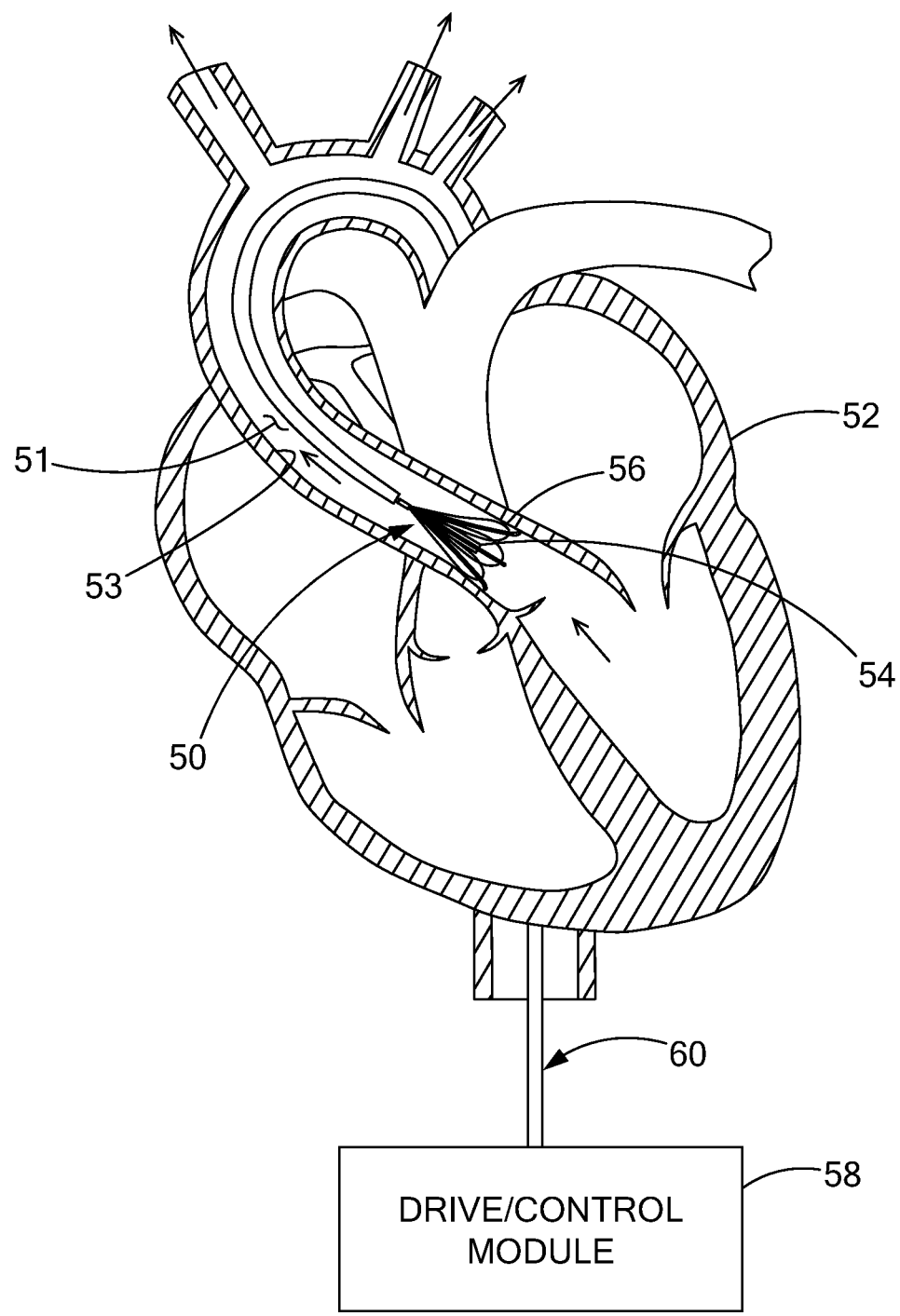
FIG. 1 is a cross-sectional environmental view of a ventricular assist device in a human heart in accordance with an embodiment of the present disclosure.

Referring to FIG. 1, a ventricular assist device 50 according to the teachings of the present disclosure is placed at a target site, such as an aorta of a human heart 52, to provide left ventricular assist. It is understood that the ventricular assist device 50 of the present disclosure may be placed in places other than aorta for right ventricular assist. The ventricular assist device 50 includes an intravascular blood pump 54 and a collapsible frame 56 that receives the intravascular blood pump 54 therein. The ventricular assist device 50 is connected to an external drive/control module 58 through a cable assembly 60.

The collapsible frame 56 supports and receives the intravascular blood pump 54 and is movable between a collapsed state and an expanded state. When the collapsible frame 56 is deployed in a body cavity 51, the collapsible frame 56 is expanded radially to engage an interior wall 53 of the body cavity 51 to position the intravascular blood pump 54 at the target site. The collapsible frame 56 allows the blood to flow therethrough. When the collapsible frame 56 is in the collapsed state, the collapsible frame 56 disengages from the interior wall 53 and thus the ventricular assist device 50 may be retrieved from the body cavity 51.

Figure 2:
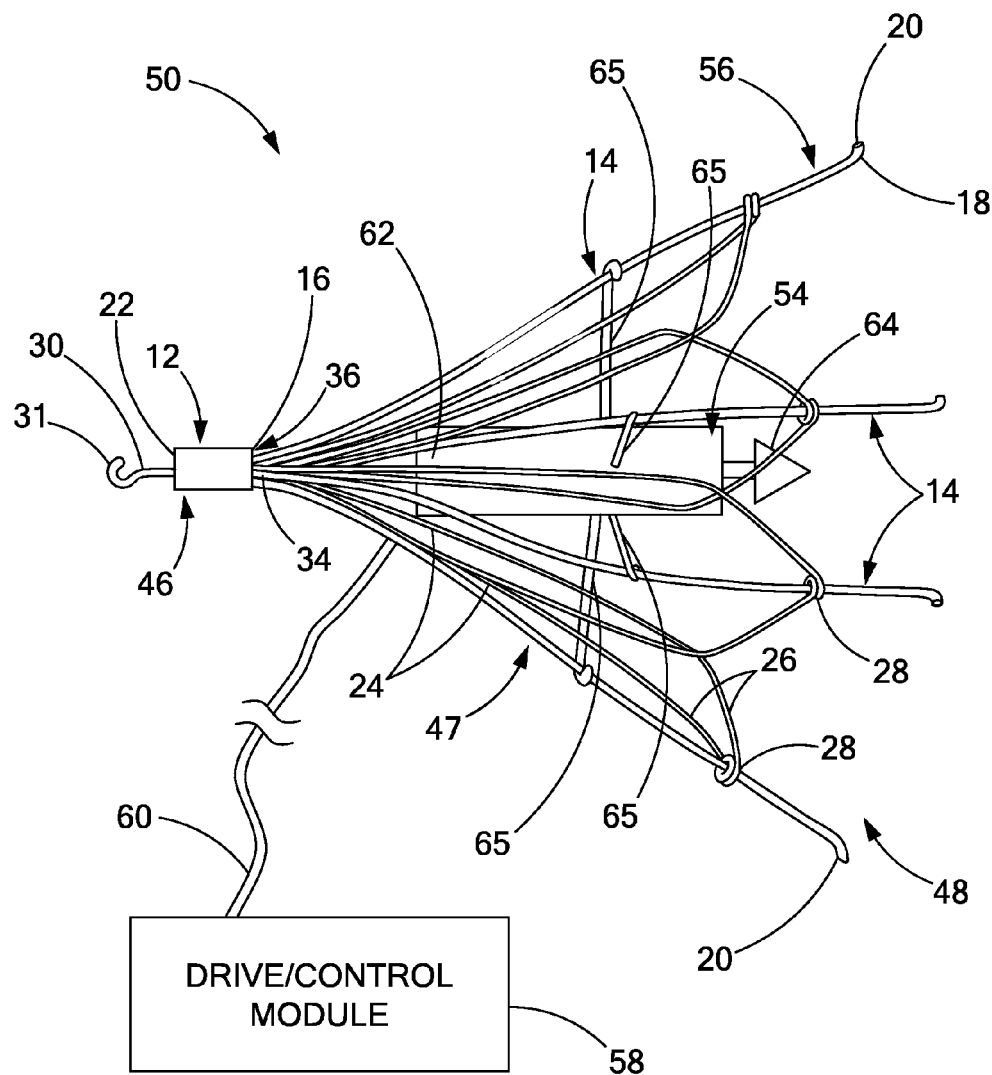
FIG. 2 is a perspective view of a ventricular assist device of FIG. 1.
Figure 3:
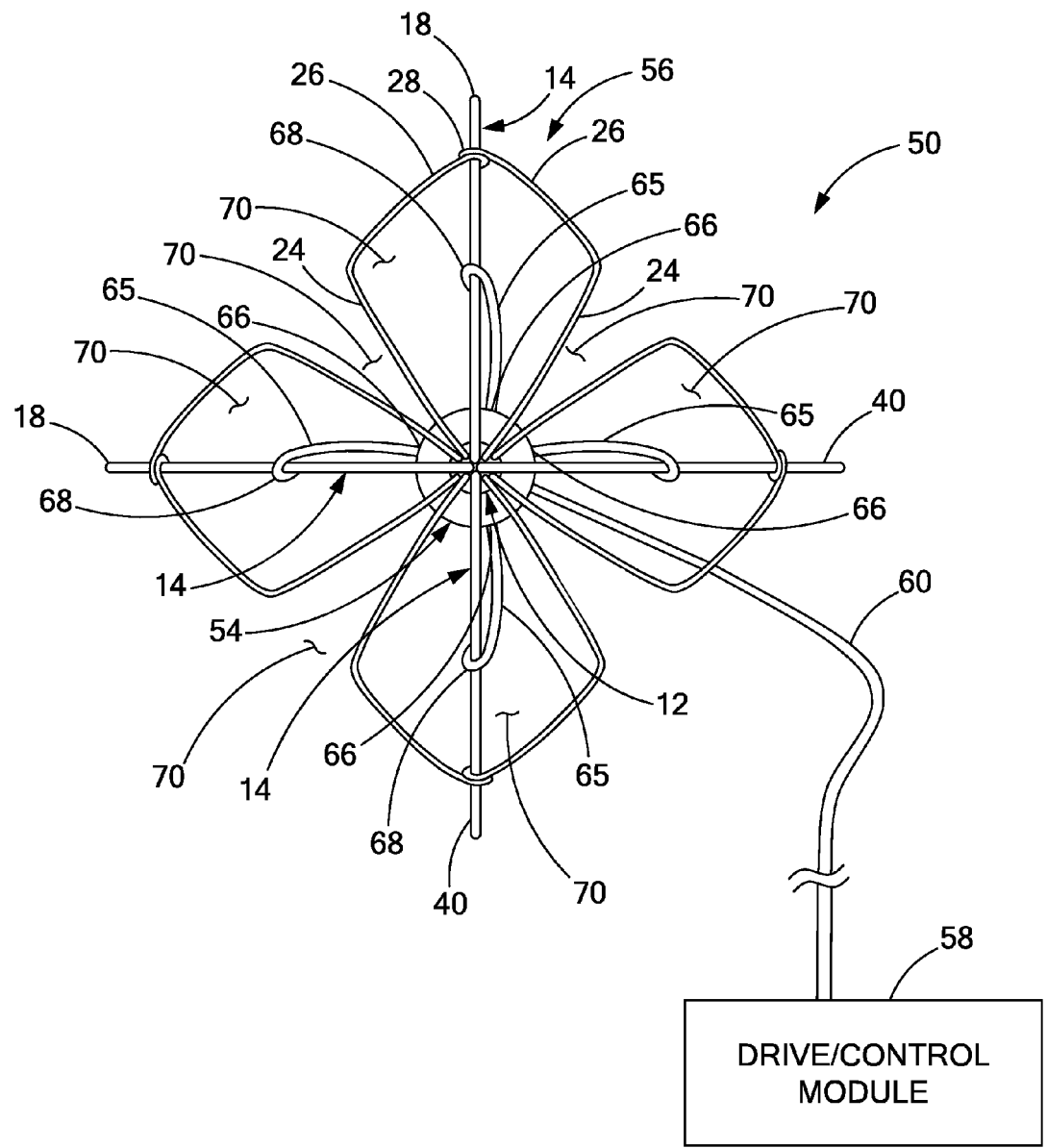
FIG. 3 is an end view of the ventricular assist device of FIG. 1.

Referring to FIGS. 2 to 3, the collapsible frame 56 according to one embodiment of the present disclosure has a framework similar to a Gunther Tulip® vena cava filter. More specifically, the collapsible frame 56, when in the expanded state, includes a proximal portion 46, a medial portion 47 and a distal portion 48. An apical hub body 12 is provided at the proximal portion 46 and has a first or distal end 16 and a second or proximal end 22. A plurality of longitudinal struts 14 extend from the apical hub body 12 to the distal portion 48 and include proximal ends 34 and distal ends. The proximal ends 34 of the longitudinal struts 14 are secured to the distal end 16 of hub body 12. The distal end portions 18 of the longitudinal struts 14 have anchoring sections 20. The longitudinal struts 14 divergingly extend distally from the distal end 16 of the hub body 12. The second or proximal end 22 of hub body 12 has a retrieval section 30 extending therefrom that terminates in a hook 31.

The collapsible frame 56 further includes pairs of side elements 24, each pair of which is associated with a longitudinal strut 14. The side elements 24 each have a proximal end 36 connected to the first end 16 of the hub body 12 and a distal end 26 extending distally from the proximal end 36 to a joining portion 28. The joining portions 28 are slidably connected to an associated longitudinal strut 14. In one embodiment, the joining portions 28 may be eyelets that surround the longitudinal struts 14 and that are slidable along the longitudinal struts 14.

Anchoring sections 20 preferably are formed as short hooks and are adapted to press slightly into the interior wall 53 of the body cavity 51 at the target site to prevent movement in the direction of blood flow. The apical hub body 12 is configured to be engaged and retrieved by a retrieval device such as a snare, which can be remotely manipulated to snatch the hook 31 of the retrieval section 30. The retrieval section 30 extends from the second or proximal end 22 of the hub body 12. The structure of the collapsible frame 56 is described in U.S. Publication No. 2002-0193828, titled "Endovascular Filter," the disclosure of which is incorporated herein by reference in its entirety.

The intravascular blood pump 54 may be any of conventional blood pumps and may include a pump frame 62, an impeller 64 protruding outwardly from the pump frame 62, and a rotary pump (not shown) received within the pump frame 62. The impeller 64 is rotatably driven by the drive/control module 58 through the cable assembly 60. The pump frame 62 seals the rotary pump from the blood.

The ventricular assist device 50 further includes a plurality of legs 65 extending from the pump frame 62 to the longitudinal struts 40. The plurality of legs 65 each include a first end 66 connected to the pump frame 62 and a second end 68 connected to the collapsible frame 56. The second ends 68 of the legs 65 are slidably attached to the plurality of longitudinal struts 14. In one embodiment, the first ends 66 of the legs 65 may each include a hinge to allow the legs 65 to be pivotable relative to the pump frame 62. The second ends 68 of the legs 65 may each include an eyelet surrounding the longitudinal struts 14 to allow the legs 65 to be slidable along the longitudinal struts 14. The plurality of legs 65 properly position the intravascular blood pump 54 inside the collapsible frame 56 while allowing the collapsible frame 56 to freely expand radially during deployment. Any conventional securing means to secure the intravascular blood pump 54 within the collapsible frame 56 can be used as long as the securing means does not interfere with free expansion of the collapsible frame 56.

When the collapsible frame 56 is in the expanded state, the intravascular blood pump 54 is properly supported within and coaxially disposed with the collapsible frame 56. The cable assembly 60 may pass through the space 70 between the longitudinal struts 14 and/or the side elements 24 to connect the intravascular blood pump 54 to the drive/control module 58.

Figure 4:
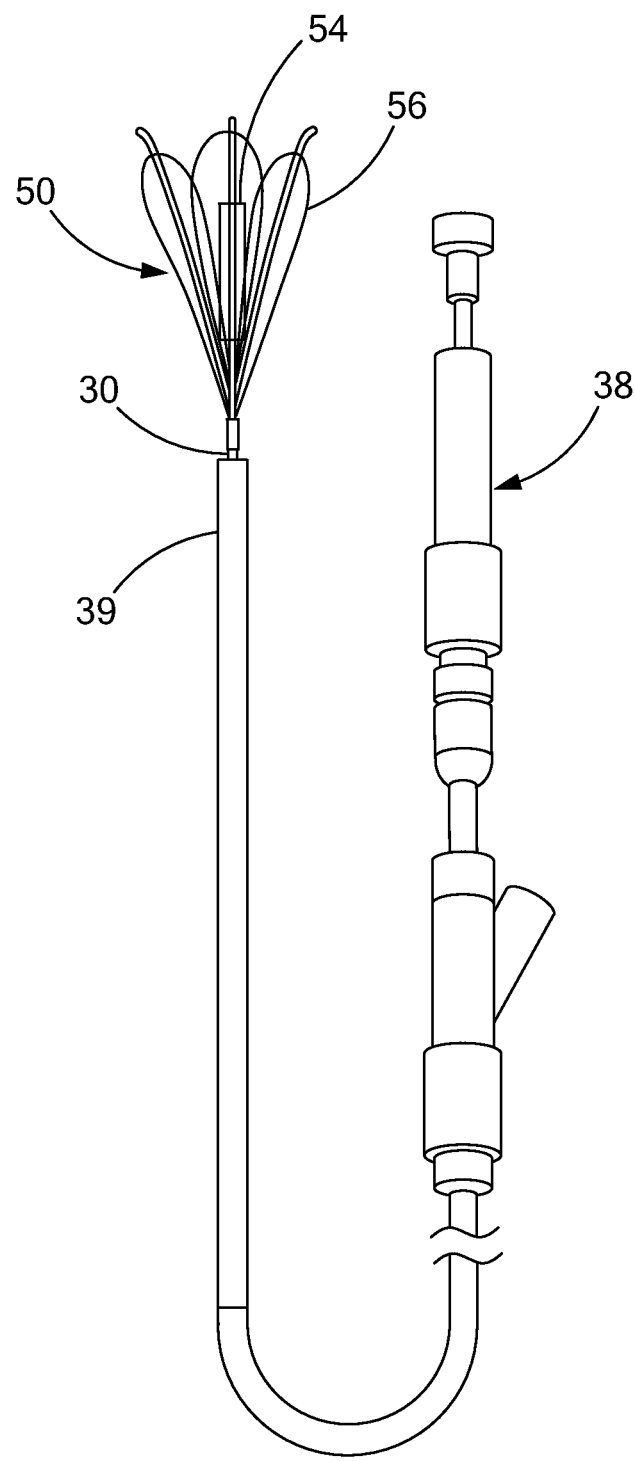
FIG. 4 illustrates the ventricular assist device of FIG. 1 being deployed from a delivery system.

Referring to FIG. 4, the ventricular assist device 50 may be deployed by a delivery and deployment system 38, particularly a sheath 39 of delivery and deployment system 38. The intravascular blood pump 54 has an elongated shape and a size smaller than the inside diameter of the sheath 39. The collapsible frame 56 is configured to be capable of collapsing back to a size smaller than the inside diameter of the sheath 39 to be "swallowed" by the sheath 39.

At some point after implantation of the ventricular assist device 50, the heart of the patient may recover and resume its normal function and ventricular assist is no longer needed. With the collapsible frame 56 of the present disclosure, it is relatively easy to collapse the collapsible frame 56, withdraw the collapsible frame 56 into the sheath and retrieve the ventricular assist device 50.

Figure 5:
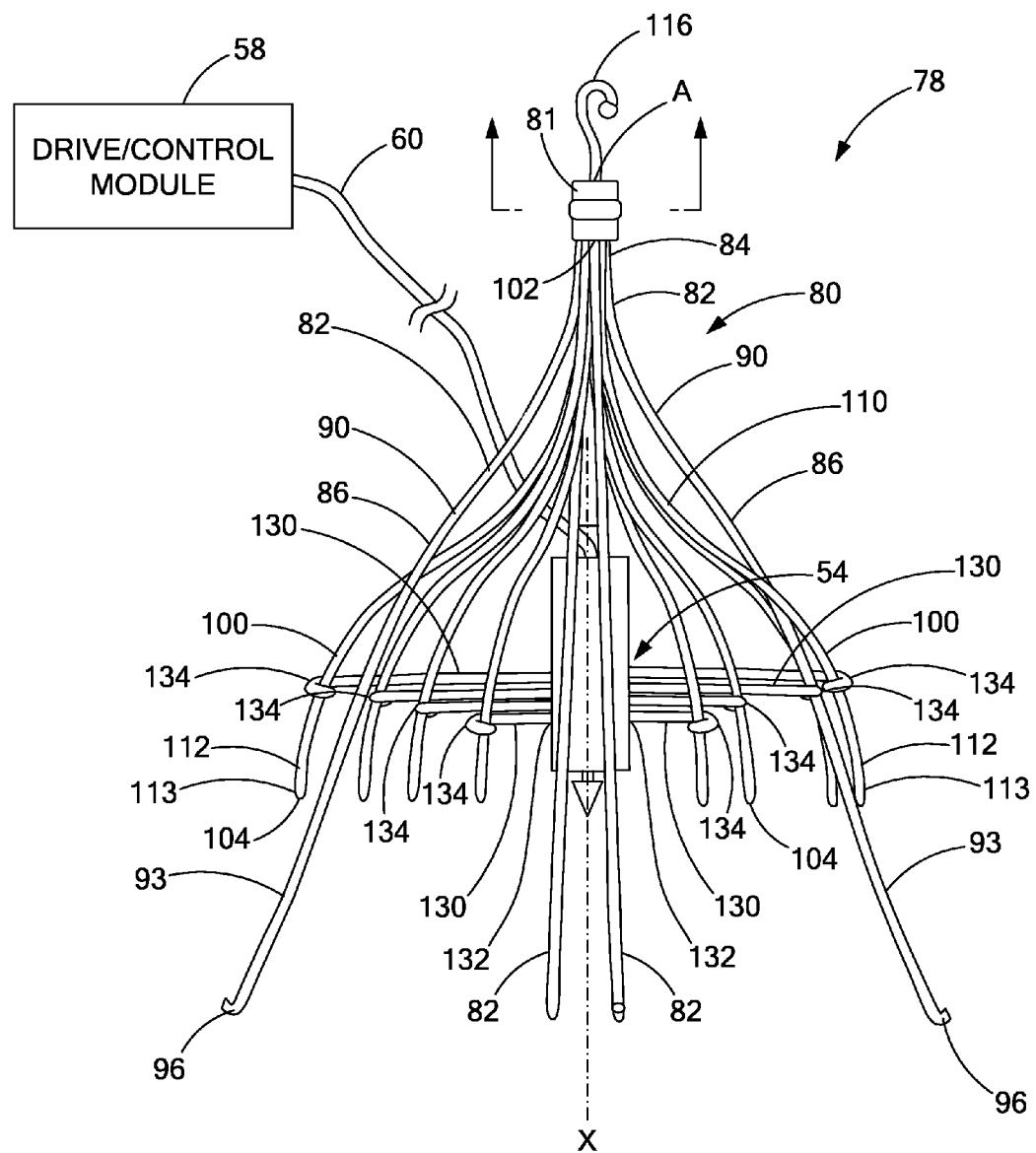
FIG. 5 is a perspective view of a ventricular assist device in accordance with another embodiment of the present disclosure.

Referring to FIG. 5, a ventricular assist device 78 in accordance with another embodiment of the present disclosure includes a collapsible frame 80 and an intravascular blood pump 54. The collapsible frame 80 has a structure similar to a celect™ vena cava filter and is movable between a collapsed state and an expanded state. The collapsible frame 80 includes a hub 81, a plurality of primary longitudinal struts 82, and a plurality of secondary longitudinal struts 100. The plurality of primary and secondary longitudinal struts 82 and 100 extend from the hub 81. The plurality of primary longitudinal struts 82 each have first ends 84 that are crimped together by the hub 81 at a center point A.

When the collapsible frame 80 is in the expanded state, the primary longitudinal struts 82 each include an arcuate segment 86 having a soft S-shape. Each arcuate segment 86 is formed with a first curved portion 90 and a second curved portion 93. The first curved portion 90 is configured to softly bend away from the longitudinal or central axis X of the collapsible frame 80, whereas the second curved portion 93 is configured to softly bend toward the longitudinal axis X.

The primary longitudinal struts 82 include anchoring hooks 96 at the distal ends. When the collapsible frame 80 is deployed and expanded in the body cavity, the anchoring hooks 96 engage the interior wall 53 of the blood cavity 51 to define a first axial position to secure the ventricular assist device 78 in the body cavity 51.

The secondary longitudinal struts 100 function to centralize the collapsible frame 80 in the expanded state in the body cavity 51. The plurality of secondary longitudinal struts 100 have connected ends 102 and free ends 104. The connected ends 102 are disposed adjacent to and extend distally from the hub 81. The connected ends 102 are crimped together at the center point A by the hub 81. Two secondary longitudinal struts 100 may be arranged in a side-by-side relationship with adjacent one of the primary longitudinal struts 82. Two secondary longitudinal struts 100 are located on each side of one primary longitudinal strut 82 to form a part of a netting configuration of the collapsible frame 80.

In this embodiment, each of the secondary longitudinal struts 100 is formed of a first arc 110 and a second arc 112. The first arc 110 extends from the connected end 102 away from the longitudinal axis X. The second arc 112 extends distally from the first arc 110 towards the longitudinal axis X. When freely expanded, free ends 104 of the secondary longitudinal struts 100 will expand radially outwardly to engage the vessel wall. When the collapsible frame 80 is in the expanded state, the first arcs 110 of the secondary longitudinal struts 100 are provided inside the first curved portions 90 of the primary longitudinal struts 82. The second arcs 112 of the secondary longitudinal struts 100 are located farther away from the central axis X of the ventricular assist device 78 than the adjacent portions of the primary longitudinal struts 82.

The free ends 104 of the secondary longitudinal struts 100 engage the interior wall 53 of the body cavity 51 to define a second axial position where the vessel wall is engaged. The second arcs 112 of the secondary longitudinal struts 100 are configured to have substantially straight portions 113 adjacent to the free ends 104 when in the expanded state so that the straight portions 113 each establish a line contact, rather than a point contact, with the interior wall 53 of the body cavity 51. The secondary longitudinal struts 100 function to stabilize the position of the collapsible frame 80 about the center of the blood cavity 53 when the collapsible frame 80 is deployed. As a result, the collapsible frame 80 has two layers or portions of struts longitudinally engaging the interior wall 53 of the body cavity 51. The length of the collapsible frame 80 is defined by the length of the primary longitudinal struts 82. As shown, a removal hook 116 extends from hub 81 opposite the primary and secondary longitudinal struts 82 and 100.

The primary longitudinal struts 82, the secondary longitudinal struts 100, and the hub 81 may be formed of a superelastic material, stainless steel wire, Nitinol, cobalt-chromium-nickel-molybdenum-iron alloy, cobalt-chrome alloy or any other suitable material that will result in a self-expanding frame. The primary longitudinal struts 82, the secondary longitudinal struts 100 and the hub 81 may be made of the same material to minimize the possibility of galvanic corrosion or molecular changes in the material due to welding. It is understood that the primary and secondary longitudinal struts 80 and 100 and the hub 81 may be made of different materials.

The ventricular assist device 78 further includes a plurality of legs 130 extending from the intravascular blood pump 54 to the collapsible frame 80 for supporting the intravascular blood pump 54 inside the collapsible frame 80. The plurality of legs 130 each include a first end 132 attached to the intravascular blood pump 54 and a second end 134 attached to the collapsible frame 80. The first ends 132 may include hinges so that the plurality of legs 130 are pivotable around the hinges. The second ends 134 may include eyelets 136 surrounding the secondary longitudinal struts 100 so that the legs 130 are slidable along the length of the secondary longitudinal struts 100. A cable assembly 60 may pass through the space between the primary and second longitudinal struts 82 and 100 to connect the intravascular blood pump 54 to a drive/control module 58.

While not shown in the drawings, it is understood that the second ends 134 of the legs 130 may be attached to the primary longitudinal struts 82 so that the legs 130 are slidable along the primary longitudinal struts 82.

Figure 6:
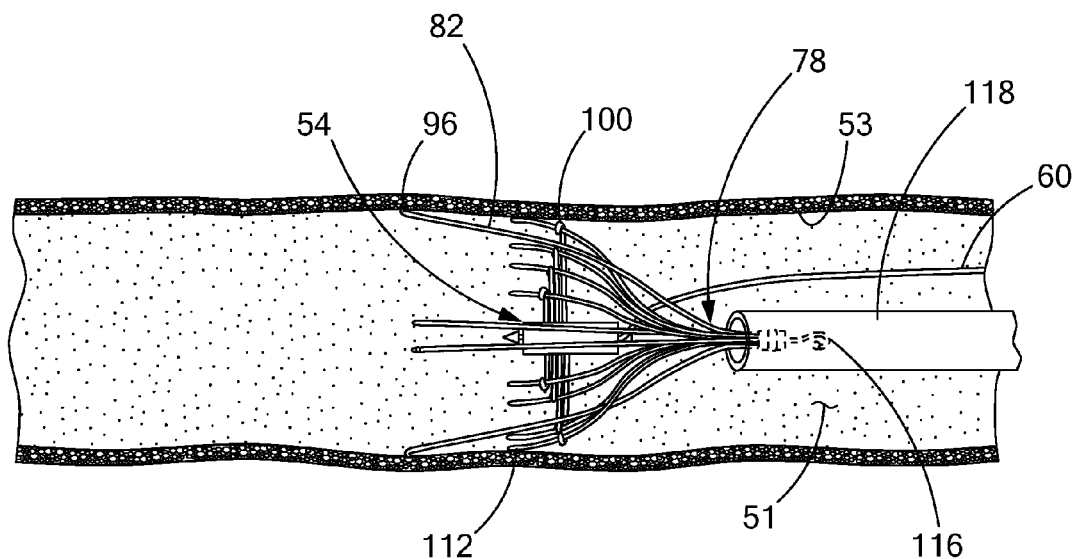
FIG. 6 is a cross-sectional view of the ventricular assist device of FIG. 5 being deployed from a delivery system into a body cavity.

Referring to FIG. 6, during deployment, the secondary longitudinal struts 100 expand first to centralize or balance the collapsible frame 80 within the body cavity 51. When the free ends of the secondary longitudinal struts emerge from the distal end of the delivery tube 118, the secondary longitudinal struts 100 expand to an expanded position. The second arcs 112 of the secondary longitudinal struts 100 engage the interior wall 53 of the body cavity 51. The second arcs 112 of the secondary longitudinal struts 100 function to stabilize the attitude of collapsible frame 80 and the ventricular assist device 78 about the center of the body cavity 51. The collapsible frame 80 may be pushed further by a pusher wire (not shown) until it is fully deployed.

When the collapsible frame 80 is fully expanded in the body cavity, the anchoring hooks 96 of the primary longitudinal struts 82 and the second arcs 112 of the secondary longitudinal struts 100 are in engagement with the interior wall 53. The anchoring hooks 96 of the primary longitudinal struts 82 have anchored the collapsible frame 80 at the location of deployment in the vessel, preventing the collapsible frame 80 from moving with the blood flow through the vessel. The collapsible frame 80 is supported by two sets of struts 82 and 100 that are spaced axially along the length of the collapsible frame 80.

Figure 7:
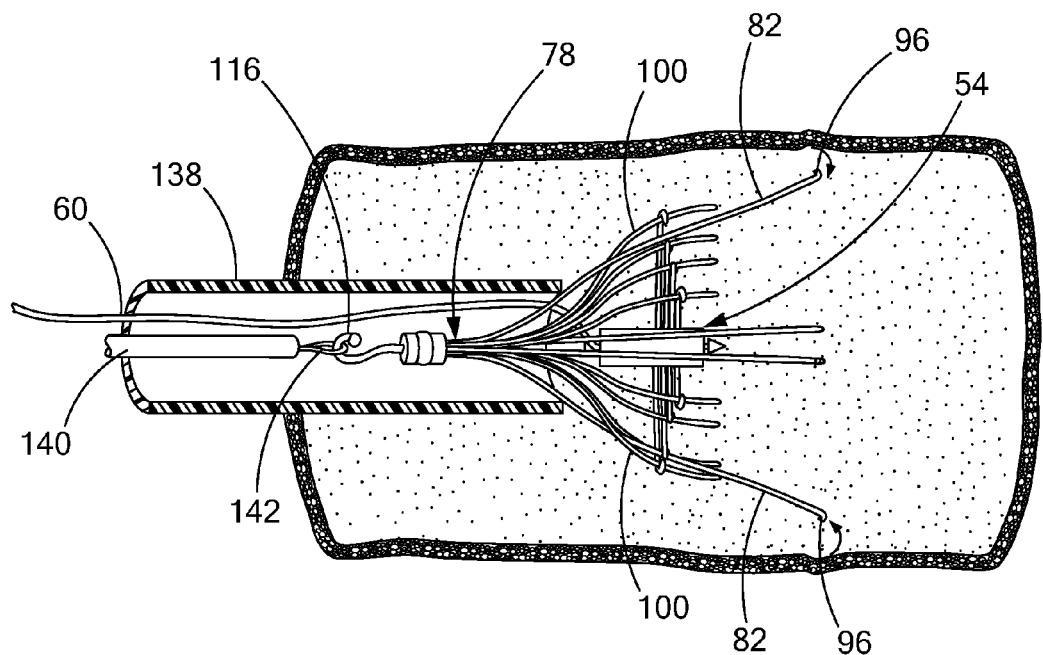
FIG. 7 is a cross-sectional view of the ventricular assist device of FIG. 5 being retrieved by a retrieval device from a body cavity.
Figure 8:
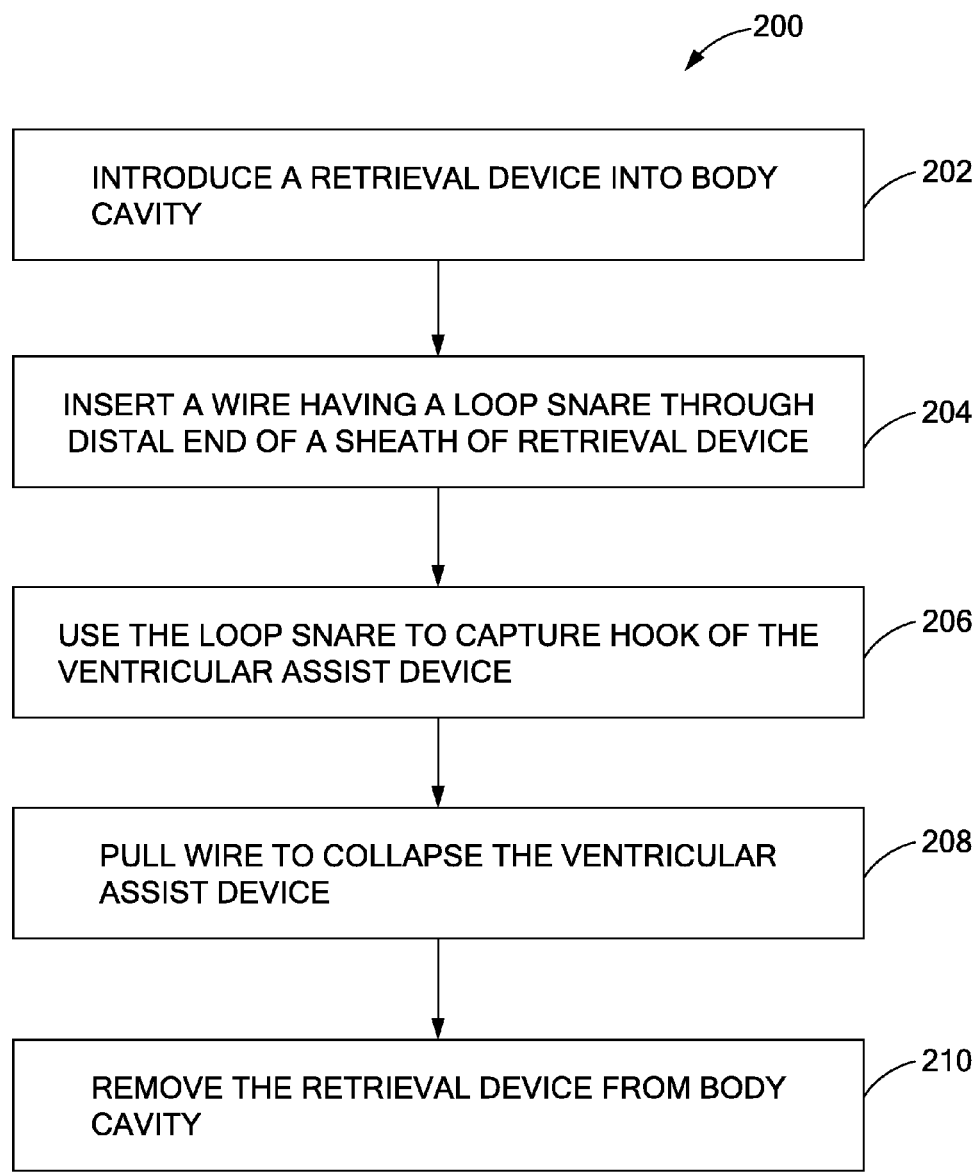
FIG. 8 is a flowchart illustrating a method of retrieving a ventricular assist device in accordance with the teachings of the present disclosure.

Referring to FIGS. 7 and 8, a method 200 of retrieving a ventricular assist device starts with introducing a retrieval device into the body cavity 51 in step 202. In this procedure, a removal catheter or sheath 138 of the retrieval device is inserted into the superior vena cava. In step 204, a wire 140 having a loop snare 142 is inserted through the distal end of the sheath 138 of the retrieval device. The wire 140 is then manipulated by any suitable means from the proximal end of the retrieval device. In step 206, the loop snare 142 captures the hook 116 of the ventricular assist device 78. In step 208, the wire 140 is pulled while pushing the sheath 138 so that the sheath 138 is passed over the collapsible frame 80 to collapse the ventricular assist device 78. When the ventricular assist device 78 is received within the sheath 138 of the retrieval device, the retrieval device is removed from the body cavity 51 in step 210.

With the collapsible frame of the present disclosure, the ventricular assist device can be retrieve without difficulty or complication after being implanted. The intravascular blood pump does not contact the interior wall of the body cavity during implantation.

While the ventricular assist device has been described to have a collapsible frame with a framework similar to that of a Gunther Tulip® or a Celect™ vena cava filter, it is understood that a collapsible frame of any configurations may be used as long as the collapsible frame can support and receive the intravascular blood pump therein. For example, the frame may be a regular stent-like frame, including but not limited to, a Z-stent and Cook Medical's Zilver binary stent. Zilver binary stent is made of flexible laser-cut nitinol tubing and allows Zilver to conform to the ductal wall while providing reliable patency.

This description is merely exemplary in nature and, thus, variations that do not depart from the gist of the disclosure are intended to be included within the scope of the disclosure. Further areas of applicability of the present invention will become apparent from the detailed description provided hereinafter. It should be understood that the description and specific examples, while indicating the preferred embodiments of the invention, are intended for purposes of illustration only and are not intended to limit the scope of this disclosure.

The invention claimed is:

1. A ventricular assist device comprising:
an intravascular blood pump; and
a collapsible frame receiving the intravascular blood pump therein and movable between a collapsed state and an expanded state,
wherein the collapsible frame engages an interior wall of a body cavity when in the expanded state and is retrievable from the body cavity in the collapsed state,
wherein the collapsible frame includes a proximal end, a distal end, and a plurality of longitudinal struts extending from the proximal end to the distal end, the plurality of longitudinal struts expanding radially when the collapsible frame is deployed in the body cavity, and
wherein the intravascular blood pump is attached to the plurality of longitudinal struts by a plurality of legs attached to the blood pump and slidable along the plurality of longitudinal struts.

2. The ventricular assist device of claim 1, wherein the connecting legs are pivotably mounted to the intravascular blood pump.

3. The ventricular assist device of claim 1, wherein the connecting legs each include an eyelet attached to the longitudinal struts.

4. The ventricular assist device of claim 1, wherein the collapsible frame allows blood to flow through.

5. The ventricular assist device of claim 1, wherein the collapsible frame includes a proximal end and a hook formed at the proximal end, the hook being engageable by a retrieval device.

6. The ventricular assist device of claim 5, further comprising a hub including a proximal end and a distal end.

7. The ventricular assist device of claim 6, wherein the hook is connected to the proximal end of the hub and the intravascular blood pump is provided adjacent to the distal end of the hub.

8. The ventricular assist device of claim 1, wherein the intravascular blood pump includes a pump frame that seals rotating components therein from blood and a plurality of legs connecting the pump frame to the collapsible frame.

9. The ventricular assist device of claim 1, wherein upon deployment, the longitudinal struts extend at oblique angles relative to each other in locations in which the plurality of legs is slidable along the plurality of longitudinal struts.

10. The ventricular assist device of claim 1, wherein the intravascular blood pump is attached to the plurality of longitudinal struts only by the plurality of legs slidable along the plurality of longitudinal struts.

11. A method of retrieving a ventricular assist device according to claim 1, the method comprising:
inserting a retrieval device into a body cavity; and
collapsing the ventricular assist device within the retrieval device.

12. The method of claim 11 further comprising inserting a wire to capture the ventricular assist device.

13. The method of claim 12 wherein the wire has a snare hoop to capture a hook of the ventricular assist device.

14. The method of claim 12 further comprising pushing a distal end of the wire through a sheath of the retrieval device to capture the hook.

\* \* \* \* \*